United States Patent [19]

Davis

[11] 4,035,514

[45] July 12, 1977

[54] WATER WASHABLE PETROLATUM COMPOSITIONS

[75] Inventor: Ronald Ivey Davis, Wilmington, Del.

[73] Assignee: ICI United States Inc., Wilmington, Del.

[21] Appl. No.: 658,833

[22] Filed: Feb. 17, 1976

[51] Int. Cl.$^2$ .................... A61K 9/06; C09D 3/00; C10M 5/12
[52] U.S. Cl. .................... 424/365; 106/285; 252/DIG. 5; 252/DIG. 8; 252/11; 252/52 A; 252/170; 252/316; 424/358
[58] Field of Search ............ 424/365, 70; 252/11, 252/52 A, 170, DIG. 5, DIG. 8, 316; 106/285

[56] References Cited

U.S. PATENT DOCUMENTS

| | | | |
|---|---|---|---|
| 3,210,248 | 10/1965 | Feldmann et al. | 424/365 |
| 3,419,665 | 12/1968 | Lachampt et al. | 424/365 |
| 3,424,849 | 1/1969 | Conklin et al. | 424/365 |
| 3,514,515 | 5/1970 | Woolf | 424/365 X |
| 3,535,427 | 10/1970 | Millar et al. | 424/365 |
| 3,835,169 | 9/1974 | Kraft et al. | 424/365 X |
| 3,846,556 | 11/1974 | Handjani et al. | 424/365 X |
| 3,919,430 | 11/1975 | Siegel | 424/365 |

*Primary Examiner*—Sam Rosen
*Assistant Examiner*—Vera C. Clarke

[57] ABSTRACT

Petrolatum containing up to 30 percent by weight of a combination dispersing agent comprising cetyl alcohol, lanolin alcohols and alkoxylated fatty acid esters of sorbitol can be dispersed in water without the use of additional soaps or detergents.

4 Claims, No Drawings

WATER WASHABLE PETROLATUM COMPOSITIONS

This invention relates to a petrolatum useful in pharmacological applications, lubricating greases, metal polishes, release agents and protective coatings. More particularly, it is an improved petrolatum composition which can be easily dispersed in water without the use of additional soaps or dispersing agents. Most particularly, it is directed to a cosmetic composition which is useful as a skin cleansing or conditioning agent.

Heretofore, petrolatum, either the white or yellow grade, while providing many beneficial effects to skin has been somewhat unpleasant to apply manually because of its difficultly removable properties. Hands used to apply the petroleum jelly usually remain greasy and require a substantial amount of soap and water for its removal. Furthermore, clothing with which it comes into contact remains greasy and difficult to clean. The composition of the present invention allows for all the beneficial effects previously derived from the use of petroleum while eliminating the unpleasantness associated with the removal of excess from the hands or clothing since it is easily water dispersable.

Petrolatum, otherwise known as mineral fat, petroleum jelly or mineral jelly, is a colorless or amber colored translucent semi-solid amorphous mass whose consistency varies with temperature. The material has a specific gravity ranging from 0.815–0.880 at 60° C. and a melting point ranging from 38°–60° C. Its chief constituents are hydrocarbons and olefins having 16–32 carbon atoms.

This material is rendered easily water dispersable by blending together a petrolatum composition having by weight 1 to 5 percent cetyl alcohol; 1 to 4 percent lanolin, hydroxylated lanolin, or lanolin alcohols and 10 – 20 percent ethoxylated sorbitol oleic acid esters such as 40 dendro sorbitol septaoleate (a composition prepared by reacting sorbitol containing 15% water with 7 molar equivalents of oleic acid and thereafter 40 molar equivalents of ethylene oxide) or 40 dendro sorbitol hexaoleate (a composition prepared by reacting sorbitol containing 15% water with 6 mols oleic acid and thereafter with 40 mols of ethylene oxide).

While the above concentration ranges are preferred in making a blend having a viscosity similar to that of the unblended petrolatum more or less of the additives can be employed to render the blend more or less viscous. The addition of more cetyl alcohol renders the composition unstable in that the alcohol tends to separate. Addition of greater amounts of lanolin softens the product while lowering the viscosity. The use of greater amounts of sorbitol oleate emulsifiers do not substantially increase the water dispersability of the blend to justify the additional cost.

While the prior art discloses the use of each of the named dispersing agents, as for example on page 33 of a pamphlet entitled "Atlas Products For Cosmetics and Pharmaceuticals" or on page 8 of a pamphlet entitled "Emulsification of Basic Cosmetic Ingredients" singly in combination with petrolatum to provide soap and water washable combinations, their combined use to provide an easily water-only washable combination is considered to be unexpected.

The unique blends of ingredients are made by measuring out the appropriate quantities, heating until a uniform blend is obtained and thereafter permitting the mix to cool to a viscous salve or cream. Blends having the following compositions exemplify the invention:

EXAMPLE 1

|  | Wt., % |
|---|---|
| Petroleum jelly | 80 |
| Cetyl alcohol | 3 |
| Lanolin alcohols | 2 |
| Polyoxyethylene sorbitol hexaoleate | 15 |
|  | 100 |

Preparation: Heat all ingredients with stirring until homogeneous. Cool without agitation to set point.

EXAMPLE 2

|  | Wt., % |
|---|---|
| Petroleum jelly | 80 |
| Cetyl alcohol | 3 |
| Lanolin | 2 |
| Polyoxyethylene sorbitol hexaoleate | 15 |
|  | 100 |

Preparation: Same as Example 1.

EXAMPLE 3

|  | Wt., % |
|---|---|
| Petroleum jelly | 80 |
| Cetyl alcohol | 3 |
| Lanolin | 2 |
| Polyoxyethylene sorbitol septaoleate | 15 |
|  | 100 |

Preparation: Same as Example 1.

Included within the scope of the invention are compositions containing minor amounts of perfumes, dyes, coloring agents, anticeptics, preservatives and medically active ingredients.

What is claimed is:

1. A water washable petrolatum composition comprising 70–90 percent petrolatum, 1–5 percent cetyl alcohol, 1–4 percent lanolin or lanolin alcohols and 10–20 percent of ethoxylated sorbitol oleic acid esters selected from the group consisting of 40 dendro sorbitol septaoleate and 40 dendro sorbitol hexaoleate.

2. The composition of claim 1 comprising 80 percent petrolatum, 3 percent cetyl alcohol, 2 percent lanolin alcohols and 15 percent 40 dendro sorbitol hexaoleate.

3. The composition of claim 1 comprising 80 percent petrolatum, 3 percent cetyl alcohol, 2 percent lanolin and 15 percent 40 dendro sorbitol hexaoleate.

4. The composition of claim 1 comprising 80 percent petrolatum, 3 percent cetyl alchol, 2 percent lanolin and 15 percent 40 dendro sorbitol septaoleate.

UNITED STATES PATENT AND TRADEMARK OFFICE
CERTIFICATE OF CORRECTION

PATENT NO. : 4,035,514
DATED : July 12, 1977
INVENTOR(S) : Ronald Ivey Davis

It is certified that error appears in the above-identified patent and that said Letters Patent are hereby corrected as shown below:

Column 1, line 21, "petroleum" should read -- petrolatum --.

Signed and Sealed this

Twenty-fourth Day of April 1979

[SEAL]

Attest:

RUTH C. MASON
Attesting Officer

DONALD W. BANNER
Commissioner of Patents and Trademarks